United States Patent [19]

Teng

[11] Patent Number: 4,820,811

[45] Date of Patent: Apr. 11, 1989

[54] AMINE REACTED THERAPEUTIC AGENTS

[75] Inventor: Lin-nar L. Teng, Bothell, Wash.

[73] Assignee: Research Corporation, New York, N.Y.

[21] Appl. No.: 937,655

[22] Filed: Dec. 4, 1986

Related U.S. Application Data

[60] Division of Ser. No. 804,214, Dec. 3, 1985, Pat. No. 4,654,327, which is a division of Ser. No. 720,664, Apr. 8, 1985, Pat. No. 4,604,376, which is a continuation-in-part of Ser. No. 370,155, Apr. 21, 1982, Pat. No. 4,510,135, which is a continuation-in-part of Ser. No. 452,493, Dec. 23, 1982, Pat. No. 4,582,820.

[51] Int. Cl.$^4$ .................. C08B 37/10; C07K 5/00
[52] U.S. Cl. ............................. 536/21; 435/183;
435/189; 435/216; 435/219; 530/300; 530/303;
530/306; 530/307; 530/308; 530/309; 530/311;
530/312; 530/313; 530/350; 530/380; 530/381;
530/382
[58] Field of Search ............... 530/300, 350, 303, 306;
536/21; 435/183

[56] References Cited

U.S. PATENT DOCUMENTS

| | | |
|---|---|---|
| 3,088,868 | 5/1963 | Windsor . |
| 3,506,642 | 4/1970 | Koh et al. . |
| 3,522,346 | 7/1970 | Chang . |
| 3,577,534 | 5/1971 | Koh et al. . |
| 3,844,989 | 10/1974 | Harumiya et al. . |
| 3,846,353 | 11/1974 | Grotta . |
| 4,239,754 | 12/1980 | Sache et al. . |
| 4,265,927 | 5/1981 | Ericksson et al. . |

Primary Examiner—Sam Rosen
Attorney, Agent, or Firm—Scully, Scott, Murphy & Presser

[57] ABSTRACT

A complex of a therapeutic agent is disclosed in which the therapeutic agent is complexed to an ammonium ion selected from the group consisting of

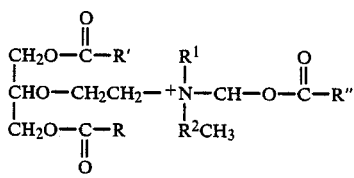

where
$R^1$ and $R^2$ are the same or different and are alkyl or hydroxy substituted alkyl containing 1 to 6 carbon atoms; and
R, R' and R" are the same or different and are saturated or unsaturated aliphatics containing at least 10 carbon atoms,

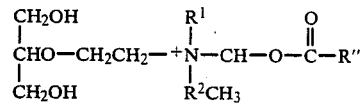

where $R^1$, $R^2$ and R" are as defined above,

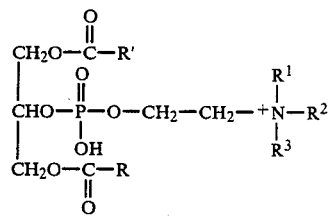

where $R^3$ is independently alkyl or hydroxy substituted alkyl containing at least 10 carbon atoms; and $R^1$, $R^2$, $R^3$ and R' having the meanings given above; and

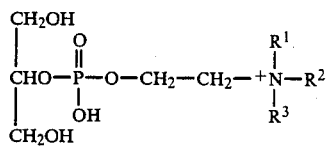

where $R^1$, $R^2$ and $R^3$ have the meanings given above. The therapeutic agent is heparin, a biologically active peptide or protein or an antineoplastic drug. The therapeutic agent may also be covalently bonded to a triglyceride type backbone to form a compound. The compound thus formed has a structural formula selected from the group consisting of

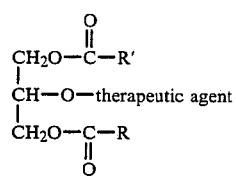

where R and R' are the same or different and are saturated or unsaturated aliphatic containing at least 10 carbon atoms; and

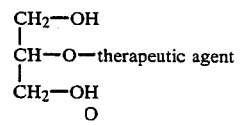

1 Claim, No Drawings

AMINE REACTED THERAPEUTIC AGENTS

This is a division of U.S. patent application, Ser. No. 804,214 filed Dec. 3, 1985, now U.S. Pat. No. 4,654,327 which is a division of U.S. patent application, Ser. No. 720,664 filed Apr. 8, 1985, now U.S. Pat. No. 4,604,376 which is a continuation-in-part of U.S. patent application, Ser. No. 370,155 filed Apr. 21, 1982, now U.S. Pat. No. 4,510,135 which is a continuation-in-part of U.S. patent application, Ser. No. 452,493, filed Dec. 23, 1982, now U.S. Pat. No. 4,582,820.

BACKGROUND OF THE INVENTION

1. Field of the Invention

The present invention relates to pharmaceutical preparations of heparin, biologically active peptides and proteins and antineoplastic drugs suitable for enteral administration.

2. Description of the Prior Art

As a result of recent progress in the field of biochemistry, many biologically active compounds such as heparin, proteins and antineoplastic drugs are now available for clinical use. However, because these compounds possess low lipophilicity and can be destroyed in the gastrointestinal tract by enzymes by cleavage and in the stomach by acid hydrolysis, methods of administering these compounds orally have not kept pace with their synthesis and identification. Typical of this situation is the case of insulin. It has long been established that insulin is an effective endogenous hormone useful in the treatment of diabetes mellitus. Furthermore, the intact insulin molecule is known to pass through the intestinal wall of various animals under specified conditions. However, adult animals (including humans) absorb insulin poorly when it is orally administered. This is probably due to a combination of factors: destruction of intact insulin molecules as previously discussed and slow passage of intact insulin molecules through the intestinal wall because of low lipophilicity. Consequently, therapeutic use of insulin is limited by the necessity of administering it parenterally, particularly by intravenous or intramuscular injection.

The desire to avoid parenteral administration of insulin has stimulated research efforts in other modes of administration, among which oral administration is the most attractive. Although efforts have been made to develop oral hypoglycemic agents other than insulin, a great deal of effort has also been concentrated on the modification of insulin in such a way that an immunologically intact and metabolically competent insulin molecule can be absorbed through the intestine so that insulin itself or a derivative thereof may be orally administered. The search in this area has been concentrated in three directions: the development of adjuvants, the co-administration of enzymatic inhibitors, and the development of liposomes. Adjuvants used with insulin include resorcinols, non-ionic surfactants such as polyoxyethylene oleyl ether, and n-hexadecyl polyethylene ether. Enzyme inhibitors include pancreatic tryspin inhibitor, diisopropylfluorophosphate (DFP), and trasylol. Liposomes include water-in-oil-in-water insulin emulsions as well as conventional liposomes.

The co-administration of enzyme inhibitors has had some degree of success, particularly when used with duodenal administration. Adjuvants such as hexylresorcinol have been administered with insulin to diabetic patients to give systemic, hypoglycemic effects. However, some adjuvants are limited to successful intra-jejunal administration. Compared to the other types of oral insulin preparations, liposomes have been relative successful. Several studies have shown systemic, hypoglycemic effects after administration of a liposome containing insulin (e.g., Patel et al, FEBS Letters, 62, 60 (1976); Hashimoto et al, Endocrinol., Japan, 26, 337 (1979)). However, liposomes are still in the development stage or their use as oral hypoglycemic agents and face continued problems of stability, shelflife, and so forth.

The difficulties of preparing other peptide and protein hormones (and other biologically active peptides and proteins) for oral ingestion or other types of enteral administration parallel the problems associated with insulin. Accordingly, there remains a need for a composition generally capable of effecting the oral administration of biologically active peptides and proteins.

Similarly it has long been established that heparin is an effective and safe blood anticoagulant. However, therapeutic use of heparin is limited by the need to administer it parenterally. A great deal of effort has been spent on the development of adjuvants, derivatives, analogs and expedients to render heparin absorbable from the intestine, so that it may be orally administered. This effort includes adjuvants such as heparin co-administered with ethylenediaminetetraacetate, EDTA (Windsor et al, "Gastrointestinal Absorption of Heparin and Synthetic Heparinoids", Nature, 190, 263-264 (1961); Tidball et al, "Enhancement of Jejunal Absorption of Heparinoid by Sodium Ethylenediaminetetraacetate in the Dog", Proc. Soc. Exp. Biol. Med., 111, 713-715 (1962); Rebar et al, "Forderung der Gastrointestinalen Resorption von Heparin durch Calciumbindungsmittel", Experimentia, 19, 141-142 (1963)), with dimethylsulfoxide, DMSO, and diethylsulfone, and their homologs (Koh, T. Y., "Intestinal Absorption of Heparin", Can. J. Biochem., 47, 951-954 (1969)); derivatives such as heparin that underwent partial desulfation and methylation (Salafsky et al, "Intestinal Absorption of a Modified Heparin", Proc. Soc. Exp. Biol. Med., 104, 62-65 (1960)) or heparinic acid and/or heparinic acid complexes (Koh et al, "Intestinal Absorption of Stable Heparin Acid Complexes, "J. Lab. Clin. Med., 80 (1), 47-55 (1972)); analogs (Jarrett et al, "Effect of Intravenous and Oral Administration of Heparinoids G 31150, G-31150-A, and of Nitrolotriacetic Acid on Blood Coagulation", Thromb. Diath Haemorrh, 25, 187-200 (1971)); and expedients, such as instillation of heparin in acidic solutions in the animal intestinal loop (Loomis, T. A., "Absorption of Heparin from the Intestine", Proc. Soc. Exp. Biol. Med., 101, 447 -449 (1959); Sue, T. K., "Heparin, Physical and Biological Factors in Absorption" in "Heparin: Structure, Cellular Functions and Clinical Applications", Ed., N. M. McDuffie, Academic Press, New York, 1979, pp. 159-166). Windsor, U.S. Pat. No. 3,088,868, discloses orally administerable heparin comprising heparin complexed with the alkali metal salts of amino acids or polyaminepolyacids, e.g., salts of EDTA. Koh et al, U.S. Pat. Nos. 3,506,642 and 3,577,534, disclose heparin complexed with weakly basic compounds ($pK_B=7.0-12.5$) being useful as an orally active medicament. However, too highly basic materials, e.g., aliphatic amines, are taught to produce materials which are not orally active. Engel et al, U.S. Pat. No. 3,574,832, discloses a heparin composition for oral, intraduodenal or rectal administration comprising heparin and a sulfate-type surfactant. Sache et al, U.S. Pat. No. 4,239,754, discloses orally active heparin compositions comprising heparin retained on or in liposomes, the lipids of said liposomes are preferably phospholipids comprising acyl chains derived from nonsaturated fatty acids.

While limited success has been achieved in the direction of increasing heparin absorbability from the intestine, these efforts have not yet reached the stage that heparin can be administered orally to give a sustaining systemic anticoagulant effect. In short, these efforts to develop an orally administered heparin for use in clinical anticoagulant therapy have so far been unsuccessful.

In related work, complexes of heparin with quaternary ammonium ions such as tridodecylmethyl ammonium chloride, TDMAC (Leininger et al, *Science*, 152, 1625 (1966); Grode et al, *J. Biomed. Mater. Res. Symp.*, 3,77 (1972)), benzalkonium chloride, BKC (Grode et al, *J. Biomed. Mater. Res. Symp.*, 3,77 (1972); Gott, U. L. *Adv. Exp. Med. Bio.*, 52 35 (1975)), and cetylpyridinium chloride, CPC (Schmer et al, *Trans. Am. Soc. Artif. Intern. Organs*, 22,654 (1976)), have been proven to render heparin soluble in organic solvents. The heparin-surfactant complexes have been successful in the coating of internal surfaces of plastic medical appliances. Chang, U.S. Pat. No. 3,522,346, discloses the preparation of non-thrombogenic microcapsules wherein the encapsulating membrane incorporates or has on its surface a quaternary ammonium-heparin complex. Suitable quaternary ammonium compounds are benzalkonium, cetyltrimethyl-ammonium and cetyldimethylbenzylammonium. Harumiya et al, U.S. Pat. No. 3,844,989, discloses antithrombogenic polymer compositions, useful in the production of medical appliances, comprising a polymer containing cationic monomer units and heparin internally bound thereto. Grotta, U.S. Pat. No. 3;846,353, discloses a method of making a non-thrombogenic plastic material by exposing the plastic to a water-insoluble, organic solvent-soluble long chain alkyl quaternary ammonium salt having 2–4 alkyl groups and then exposing the plastic to heparin. Subsequent exposure of the plastic to blood plasma failed to release heparin in an anticoagulant effective amount. Ericksson et al, U.S. Pat. No. 4,265,927, discloses a method of heparinizing the surface of a medical article by contacting the article with a complex of heparin and a cationic surfactant, preferably of the primary amine type. Marchisio et al, U.S. Pat. No. 3,865,723, discloses the use of polymers with a polyamidic-aminic structure to remove heparin from blood.

Surfactants like BKC and CPC are cationic surfactants and widely used as antimicrobials (The Extra Pharmacocopia, Matindale, 27th Ed., The Pharmaceutical Press, London (1977)) and are quite toxic, e.g., $LD_{50}$ of CPC, i.v. (mouse) is 10 mg/kg, i.v. (rat) is 6 mg/kg (Registry of Toxic Effects of Chemical Substances, U.S. Dept. HEW, 1975 Edition). Their toxicity is related to those various biological effects of quaternary ammonium heads whose effects include the depolarization of muscle tissue and hemolysis of erythrocytes. Toxic symptoms include dyspnoea and cyanosis due to paralysis of the respiratory muscles, possibly leading to asphyxia (Gastmeier et al, *Z. Ges. Gerich. Med.*, 65, 96 (1969)) and allergic reactions, after repetitive applications of quaternary ammonium salt solutions to the skin, which have been reported to occur in some patients (Morgan, J. K., *Br. J. Clin. Prac.* 22, 261 (1969); Lansdown et al, *Br. J. Derm.*, 86, 361 (1972)). It is also believed that the surfactant characteristics of the quaternary ammonium ion, particularly in the liver, causes additional alterations in a number of chemical, biological and transport phenomena (Bohr et al, "Labile Quaternary Ammonium Salt as Soft Antimicrobials", *J. Med Chem.* 23, 469–474 (1980)).

A related problem in biochemistry is to be able to contact tumor cells spread along the hymphatic pathways which metastasize in the lymph nodes with intact antineoplastic drugs and agents. Presently, such agents have been subject to the same problems discussed in the above discussion. As such contact of antineoplastics with tumor cells in the lymph nodes has not been very successful.

SUMMARY OF THE INVENTION

It is an object of this invention to provide an effective method or orally administering biologically active compounds including heparin, proteins and peptides and antineoplastic drugs.

It is a further object of this invention to provide compositions containing heparin, biologically active proteins and peptides or antineoplastic drugs which are effective when administered orally or by other enteral methods.

It is still a further object to provide a method of producing such compositions which can be carried out with heparin, biologically active peptides or proteins and antineoplastic drugs.

It is yet a further object to provide a covalent compound which permits contact with tumor cells located in the lymph nodes.

In accordance with the present invention a complex of heparin with a quaternary ammonium ion selected from the group consisting of

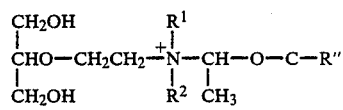

where $R^1$ and $R^2$ are the same or different and are alkyl or hydroxy substituted alkyl; and $R''$ is a saturated or unsaturated aliphatic containing at least 10 carbon atoms;

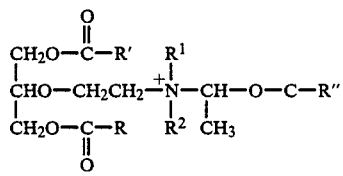

where $R^1$, $R^2$ and $R''$ have the meanings given above; and R and $R'$ are saturated or unsaturated aliphatics containing at least 10 carbon atoms;

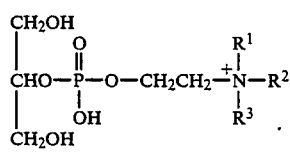

where $R^1$, $R^2$ and $R^3$ have the meanings given above; and

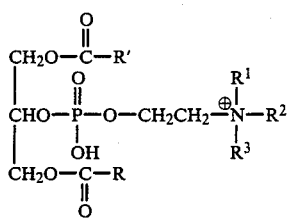

where $R^1$, $R^2$, $R^3$ and R and R' have the meanings given above.

In further accordance with the present invention a composition is disclosed comprising a sandwich complex comprising a hydrophobic core complex of a biologically active peptide or protein with an alkyl or alkenyl sulfate having 6-24 carbon atoms and 0-3 double bonds which forms an electrostatic complex with a quaternary ammonium ion selected from the group consisting of

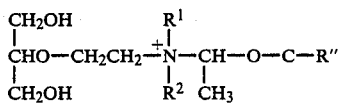

where
$R^1$ and $R^2$ are the same or different and are alkyl or hydroxy substituted alkyl; and
R'' is a saturated or unsaturated aliphatic containing at least 10 carbon atoms;

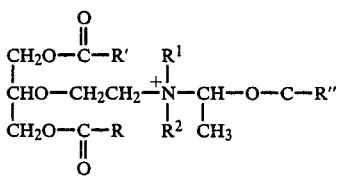

where $R^1$, $R^2$ and R'' have the meanings given above; and R and R' are saturated or unsaturated aliphatics containing at least 10 carbon atoms;

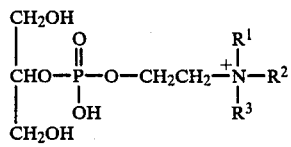

where $R^1$, $R^2$ and $R^3$ have the meanings given above; and

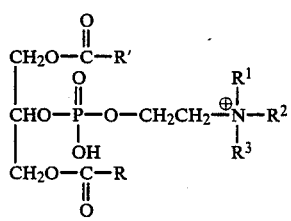

where $R^1$, $R^2$, $R^3$ R and R' have the meanings given above.

In further accordance with the present invention a compound is set forth selected from the group consisting of

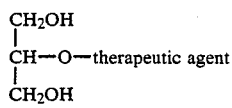

where therapeutic agent is heparin, a biologically active peptide or protein or an antineoplastic drug; and

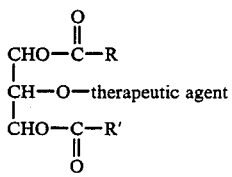

where therapeutic agent has the meanings given above; and
R and R' are the same or different and are saturated or unsaturated aliphatic containing at least 10 carbon atoms.

DESCRIPTION OF THE PREFERRED EMBODIMENTS

The present invention involves a method of modifying a biologically active compound in such a way that the compounds are absorbed into the systemic circulation when administered enterally, particularly orally, while remaining immunologically intact and metabolically competent. To achieve this result, the biologically active compound is coupled to a protective carrier in the form of a complex or covalent compound. To be successful the complex or compound must meet the following criteria: (a) it must be resistant to the acidic environment in the stomach; (b) it must be resistant to enzymatic degradation by gastric and pancreatic enzymes; (c) it must be sufficiently lipophilic to pass the intrinsic barrier of the intestinal wall; and finally (d) the changes in physiological and biological properties of the biologically active compound resulting from the modification must be minimal so that their hormonal activity is maintained. While criteria (c) and (d) are basic structural requirements for all enterally administered compounds (such as by rectal, buccal or topical routes), criteria (a) and (b) must be met in addition to (c) and (d) for the compound to be orally effective.

Specifically, in one preferred embodiment, it has been discovered that heparin forms complexes with certain "soft" or "pseudo" quaternary ammonium ions to render heparin hydrophobic and lipophilic to thereby carry heparin through the lipid barrier of the intestinal wall and, consequently, increase the absorbability of heparin from the intestine. A systemic anticoagulant effect can thereby be achieved.

It will be understood that heparin is a very complex molecule, with a structure which has not been completely elucidated. It is tentatively identified as a sulfated copolymer consisting of alternating 1-4 α linked glucosamine and glucuronic acid residues. In accordance with the invention, heparin is combined with certain quaternary ammonium ions, which in themselves are not simple. Therefore the specific structure of the resulting product cannot be stated with certainty and the terminology "complex" is used to embrace the structures which may be formed. Preferably, the complex contains five moles of the ammonium ion of this invention per mole of heparin tetrasaccharide unit, it being believed that complexation occurs with the sulfate groups of the tetrasaccharide unit. For purposes of illustration a schematic representation of the repeating heparin tetrasaccharide unit (sodium salt) is shown below

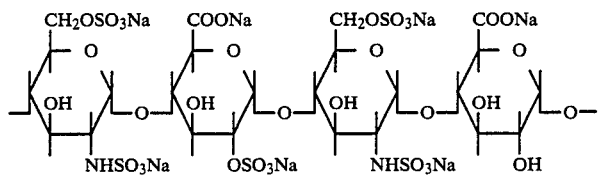

Specifically, complexes of heparin are formed with quaternary ammonium ions selecte from the group consisting of

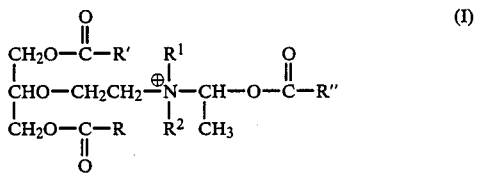

where

R$^1$ and R$_2$ are the same or different and are alkyl or hydroxy substituted alkyl containing 1 to 6 carbon atoms; and R, R' and R" are the same or different and are saturated or unsaturated aliphatics containing at least 10 carbon atoms

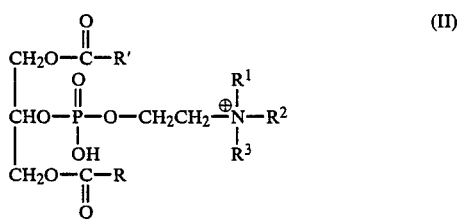

where R$^1$, R$^2$, R and R' have the meaning of ion (I) and R$^3$ is independently an alkyl or hydroxy substituted alkyl containing 1 to 6 carbon atoms:

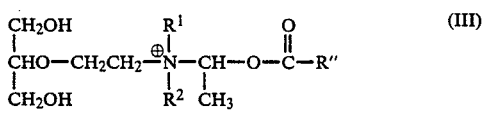

where R$^1$, R$^2$ and R" have the meanings given above and

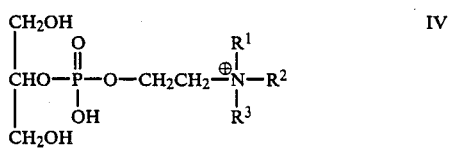

where R$^1$, R$^2$ and R$^3$ have the meanings given above.

The present invention also provides a sandwich-type complex of a biologically active peptide or protein with an alkyl sulfate and a soft quaternary ammonium ion. The biologically active peptide (hereafter "peptide" or "protein" will refer to both peptide and protein molecules unless otherwise indicated) first forms a hydrophobic core complex with the alkyl sulfate. This core complex protects the peptide molecule from acidic hydrolysis and enzymatic degradation and increases the liopophilicity of the peptide molecule, thereby allowing the intact peptide to pass through the stomach when orally ingested and to increase the rate at which it is absorbed through the intestine wall. This inner complex may be formed between the peptide molecule and the alkyl sulfate. Hydrophobic complexes of a peptide with an alkyl sulfate are generally rod-like with a helical polypeptide chain of the peptide existing within a hydrophobic shell formed by the alkyl sulfate. Typical of alkyl sulfate complexes with protein are those complexes formed with sodium dodecyl sulfate (SDS). SDS has been found to bind protein molecules in constant gram to gram ratios irrespective of nature of protein but depending on the SDS monomer concentration. When SDS monomer concentration exceeds $5 \times 10^{-4}$M, proteins form complexes with SDS in a high binding ratio where one gram of protein binds to about 1.4 gram of SDS. When the SDS monomer is less than $5 \times 10^{-4}$M, proteins form complexes with SDS in a low binding ratio where one gram of protein binds to about 0.4 gram of SDS. Both protein SDS complexes assume a similar, rod-like shape with a helical polypeptide chain or protein folded back upon itself near its middle to give a double helical rod and the SDS forming a shell about the rod via hydrophobic forces. The sulfate groups of SDS are on the surface of the rodlike complexes as evidenced by the electrophoretic migration of insulin in the presence or in the absence of SDS. In electrophoresis at pH 3 in the absence of SDS, insulin is fully protonated and migrates to cathode. In the presence of SDS (0.1%) at pH 3, insulin migrates to the anode (as if it is an anion).

Since alkyl sulfates are themselves hydolyzed to fatty acid alcohols and a sulfuric acid salt at acidities approximately those of the stomach, the rod-like peptide.alkyl sulfate complex requires an additional protective coating for oral administration which is provided by a soft quaternary ammonium ion, the structures of which are described later in detail.

By utilizing the method of the invention, it is possible to prepare peptide compositions suitable for oral administration which contain endogenous opioid agonists, such as encephalins and endorphins; hypothalmic hormones, such as gonadoliberin, melanostatin, melanoliberin, somatostatin, thyroliberin, substance P, and neurotensin; adenophypophyseal hormones, such as corticotropinm, lipotropin, melanotropin, lutropin, thyrotropin, prolactin, and somatotropin; neurohypophyseal hormones; calcitropic (thyroid) hormones, such as parathyrin and calcitonin; thymic factors, such as thymosin, thymopoietin, circulating thymic factorm and thymic humoral factor; pancreatic hormones, such insulin, glucagon, and somatostatin; gastrointestinal hormones, such as gastrin, cholecystokinin, secretin, gastric inhibitory polypeptide, vasointestinal peptide, and motillin; chorionic (placental) hormones, such as choriogonadrotropin and choriomammotropin; ovarian hormones, such as relaxin; vasoactive tissue hormones, such angiotensin and brandykinin; growth factors, such as somatomedins, epidermal growth factor, urogastrone, and nerve growth factor; hemophilia factors, such as blood clotting factors VIII and IX; enzymes, such as streptokinase, fibrinolysin, deoxyribonuclease, and asparaginase; and artificial or pseudo peptides, such as deferoxamine. Many other classes and specific types of peptide and protein hormones and other biologically active molecules are known. Peptide and protein hormones suitable for use in the present invention are disclosed in Johannes Meienhofer, "Peptide and Protein Hormones", in *Burger's Medicinal Chemistry*, 4th ed., (part II), Wolff, Ed., John Wiley and Sons (1979), which is herein incorporated by reference. Preferred hormones are those with a molecular weight of less than 7000, with insulin being especially preferred.

The listings of peptides and proteins in this application are not intended to be exclusive, and it may easily be determined by simple experimentation if any protein having biological activity can be prepared into a complex according to the invention. One simple method of testing for core complex formation involves the following steps: (1) dissolve approximately 10 mg of the biologically active peptide or protein in a small amount of water or buffer; (2) adds about 15 mg of an alkyl sulfate, fior example sodium dedecyl sulfate, mix well and allow to stand for about 5 minutes; (3) subject the resulting solution to agarose or acrylamide gel electrophoresis. The complex acts as an anion even at low pH (about 3 is a good testing point) because of the sulfate groups and migrates toward the anode. If no complex has formed, the protein will be protonated at low pH and migrate toward the cathode.

If complex formation has taken place and if the resulting core complex will itself complex with a soft quaternary ammonium ion according to the process of the present invention (infra), the biolgically active peptide is suitable for use in the present invention.

Complex formation between protein and a carrier molecule is one way to protect a protein molecule from acidic hydrolysis and enzymatic degradation and to increase the lipophilicity of the protein molecule. Depending on the carrier substances selected, formation of this complex can be via columbic interaction between protein molecule and carrier substance or via hydrophobic forces. In the proposed sandwich complex of sulfates, e.g., sodium dodecyl sulfate, are commercially available. Suitable examples of preferred linear alkyl sulfates include octyl sulfate, nonyl sulfate, decyl sulfate, undecyl sulfate, dodecyl sulfate, tridecyl sulfate, tetradecyl sulfate, pentadecyl sulfate, and hexyl sulfate. Of these, decyl sulfate, dodecyl sulfate and tetradecyl sulfate are more preferred with dodecyl sulfate being most preferred.

The alkyl sulfates are generally present initially as alkali metal salts when the initial core complex is being formed. Alkali metal salts include lithium, sodium, potassium, rubidium and cesium salts. Of these, sodium and potassium are preferred, with sodium salts being most preferred. Sodium and potassium salts of dodecyl sulfate are especially preferred, with sodium dodecyl sulfate being the most preferred alkyl sulfate salt.

The weight ratio of protein or peptide to alkyl sulfate is the weight ratio of the naturally forming complex. In a preferred embodiment, insulin is complexed with sodium dodecyl sulfate (SDS). This complex forms an insulin:SDS complex in a ratio of 1:1.4 or 1:0.4 by weight (depending on the initial ratio present) and is a hydrophobic complex. Complexes of protein with SDS are preferred to other types of complexes because a wide variety of proteins are reported to bind to an identical sulfates, e.g., sodium dodecyl sulfate, are commercially available. Suitable examples of preferred linear alkyl sulfates include octyl sulfate, nonyl sulfate, decyl sulfate, undecyl sulfate, dodecyl sulfate, tridecyl sulfate, tetradecyl sulfate, pentadecyl sulfate, and hexyl sulfate. Of these, decyl sulfate, dodecyl sulfate and tetradecyl sulfate are more preferred with dodecyl sulfate being most preferred.

The alkyl sulfates are generally present initially as alkali metal salts when the initial core complex is being formed. Alkali metal salts include lithium, sodium, potassium, rubidium and cesium salts. Of these, sodium and potassium are preferred, with sodium salts being most preferred. Sodium and potassium salts of dodecyl sulfate are especially preferred, with sodium dodecyl sulfate being the most preferred alkyl sulfate salt.

The weight ratio of protein or peptide to alkyl sulfate is the weight ratio of the naturally forming complex. In a preferred embodiment, insulin is complexed with sodium dodecyl sulfate (SDS). This complex forms an insulin:SDS complex in a ratio of 1:1.4 or 1:0.4 by amount of SDS on a gram per gram basis. See, for example, Reynolds et al., *Proc. Nat. Acad. Sci. (US)*, 66, 1002–1003 (1970) and Reynolds et al., *J. Biol. Chem.*, 245, 5161–5165 (1970). When SDS froms a complex with insulin or other protein, the hydrophobic core complex is rod-like with a helical polypeptide chain of protein existing within a hydrophobic shell formed by the SDS. This complex of protein with alkyl sulfate is referred to herein as a core complex. This term is not intended to limit the present invention, but is believed to be generally descriptive. When this core complex is itself complexed with a soft quaternary ammonium ion, an additional layer forms on the surface of the inner complex. This latter complex is referred to as an "electrostatic" complex. Nevertheless, this term additionally is not intended to be limiting of the actual physical structure that is present in the resulting complex.

As mentioned above, the inner complex is reacted with quaternary ammonium ion to form an outer complex. The phrase quaternary ammonium ion as used in this invention includes the ions having the structural formulas I–IV where $R^1$, $R^2$, $R^3$, R, R' and R" have the meanings given earlier.

The present invention is also directed to a new compound which incorporates a therapeutic agent, which may be heparin, a biologically active peptide or protein or antineoplastic drug bound to a triglyceride type backbone structure by covalent bond to form a compound which is enterically introduced into the body. This compound, like the complexes discussed above, provides a means of providing an intact bioactive material, of the types mentioned earlier into the body.

A particular advantageous feature of this embodiment is the ability to target antineoplastic drugs and agents into the lymphatic system. As those skilled in the art are aware, tumor cells often spread along the lymphatic pathways and metastasize in the lymph nodes. Thus, in a preferred embodiment the therapeutic agent covalently bonded to the triglyceride structure is an antineoplastic agent. For example, 1-asparaginase can be bonded to the triglyceride type backbone.

A triglyceride structure is covalently bonded to the therapeutic agent because it is known that the digestion of triglycerides (fat) in the lumen of intestine proceeds first by the removal of a terminal fatty acid to produce a 1,2-diglyceride. The other terminal fatty is then removed to produce a 2-monoglyceride. As pancreatic lipase is virtually specific for the hydrolysis of primary ester linkage, to remove the fatty acid from 2-monoglyceride requires its isomerization to primary ester linkage, i.e., 1-monoglyceride. The isomerization is a relatively slow process, as a result 2-monoglyceride is the major end product of fat digestion and less than 25% of the ingested fat is completely broken down to glycerol and fatty acid. Within the intestinal mucosa, 2-monoglyceride and some of 1-monoglyceride may be reconverted to triglyceride, whereas about 22% of 1-glycerides are hydrolyzed to produce free glycerol and free fatty acid which are passed directly to the portal vein. The triglycerides so synthesized will be incorporated in the form of chylomicrons which are transported into the lymphatics (the lacteals) and hence via thoracic duct into the circulating blood.

The triglyceride type backbone to which the therapeutic agent is covalently bonded results in a structural formula selected from the group

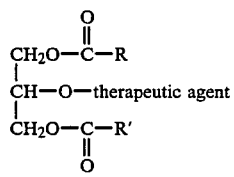
(V)

where R and R' are the same or different and saturated or unsaturated aliphatics containing at least 10 carbon atoms; and therapeutic agent may be heparin, a biologically active peptide or protein or an antineoplastic agent; and

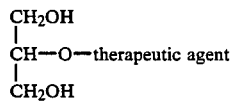
VI where therapeutic agent has the meanings given above.

Another aspect of the present invention is the ammonium ions complexed with heparin or a biological peptide or protein. One of these ammonium ions is the ion having the structural formula III. This ion is formulated by reacting glyceride with benzaldehyde in toluene in the presence of p-toluene sulfonic acid catalyst. This reaction, preferably by refluxing the reactants for about 5 hours, produces a mixture of 1,2-benzylidene glycerol, an oil and 1,3-benzylidene glycerol, a solid. The 1,3-benzylidene glycerol crystals are separated from the 1,2-benzylidene glycerol liquid.

In an alternative method, 1,3-benzylidene is formed in the absence of any other product, simplifying its recovery. In this process step hydroxyacetone is reacted with benzaldehyde using toluene solvent in the presence of a catalytic amount of p-toluene sulfonic acid.

As in the first reaction, the reaction is conducted at reflux over a period of about 5 hours. The product of this reaction is 5-oxo-2-phenyl-1,3-dioxane. In turn, the dioxane is reacted with sodium borohydride and then the reaction product is reacted in-situ with sodium hydroxide which results in the formation of 1,3-benzylidene glycerol.

Independent of the method utilized to synthesize the 1,3-benzylidene glycerol it is reacted with potassium metal to produce the potassium salt of 1,3-benzylidene glycerol oxide. The reaction is conducted in a xylene slurry of the finely divided potassium metal under reflux and stirring. The oxide is reacted with an excess of dimethylaminoethyl chloride under reflux and stirring for at least 2 hours. Upon cooling the byproduct, potassium chloride, is removed by filtration. Upon purification 1,3-benzylidene glycerol ether is formed.

The 1,3-benzylidene glycerol ether in 1,3-N,N-dimethylbenzylidene is reacted with an alpha-chloroethyl ester of a long chain saturated or unsaturated fatty acid, RC(O)OCH(CH$_3$)Cl, in petroleum ether or other suitable solvent. The reaction is conducted under a blanket of dry nitrogen gas with the reactants present in equimolar amount. The product of this reaction is 1,3-benzylidene glycerol ester. The reaction occurs under reflux and stirring.

The thus formed ester is reacted with 2-methoxyethanol in the presence of boric acid (finely divided solid) for between ½ and 1 hour. The purified product of this reaction is compound III.

To obtain the ion having te structural formula I, dihydroxy acetone is reacted with acid chloride of the desired fatty acid R—C(O)Cl in a chloride acceptor, preferably pyridine, and in chloroform solution. This reaction results in the product, diacyl acetone having the structural formula

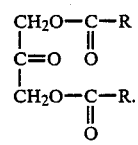

Reaction with sodium borohydride, followed by the in-situ reaction with sodium hydroxide produce 1,3-diacycl glycerol.

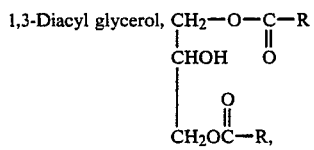

is then treated in accordance with the procedures enumerated above to produce the ion having the structural formula I.

The synthesis of the ammonium ion having the structural formula IV where $R^1$, $R^2$ and $R^3$ are each methyl is obtained by reacting 1,3-benzylidene glycerol, obtained by the procedures enumerated above, with phosphorus oxychloride in the presence of quinoline solution. The solution is water and alcohol free with chloroform being the preferred solvent. The reaction is conducted at slight elevated temperature, preferably about 35° C., for about 1 hour to produce phosphatilic acid chloride. Preferably, the reactants are provided in equimolar amounts.

The phosphatidic acid chloride is esterified by reaction with choline iodide, the iodide present in slight stoichiometric excess, in the presence of pyridine to yield 1,3-benzylidene glycerophosphoryl choline. The benyzlidene protecting group is removed by heating the 1,3-benzylidene glycerophoryl choline with powdered boric acid in 2-methoxyethanol to yield the desired 2-glycerophosphoryl choline iodide. Analogous procedures are used to produce the desired ammonium ion where $R^1$, $R^2$ and $R^3$ are alkyl or hydroxyalkyl other than methyl. Also, halides other than iodide may also be utilized.

The same procedure is utilized to form ammonium ion having the structural formula II except that the 1,3-diacyl glycerol, obtainable by methods set forth earlier, is substituted for 1,3-benzylidene glycerol.

Another aspect of the present invention involves the synthesis of the compound having the structural formula V. In this procedure 1,3-diacyl glycerol is reacted with cyanogen bromide in a polar solvent, preferably dimethyl formamide, the bromide in aqueous solution in slightly basic medium, pH of about 8.5 to produce 1,3-diacyl-2-cyano ester which reacts with the amine of the therapeutic agent to form the compound whose structural formula is V. Those skilled in the art will appreciate that the compound formed has the structural formula

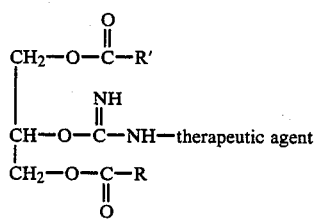

(VII)

However, for simplicity the structure of formula V has been adopted.

Obviously, the analogous compound having the structural formula VI is formed by the replacement of the starting material 1,3-diacyl glycerol with glycerol. It should also be appreciated that the actual structural formula of VI is analogous to formula VII. For simplicity, the structure VI as been adopted.

The heparin complexes of the present invention are formed by bringing heparin into contact with the desired quaternary ammonium ion. For example, an aqueous solution of heparin sodium salt is mixed with the quaternary ammonium salt, preferably the halide to give heparin-quaternary ammonium ion complexes and sodium halide. Consequently, heparin in the heparin complex is a mucopolysaccharide chain with negative sulfate groups in it associated with the positive quaternary ammonium groups, but still with sodium associated with the carboxylic acid groups. As noted above, the reaction may be conveniently performed in aqueous media. The reaction conditions are quite simple, i.e. mixing aqueous solutions of the appropriate quantity of heparin sodium salt and the quaternary ammonium salt at room temperature, preferably five moles of quaternary ammonium salt are used per mole of heparin tetrasaccharide unit. The product may be readily recovered by lyophilization, since sodium halide, the other product resulting from the above reaction, possesses no adverse effect when it is co-administered orally with the heparin complex. Alternately, the heparin-quaternary ammonium ion complex mau be separated from sodium halide by gel filtration chromatography with water as the elution solvent. Lyophilization of the elution pool that contains the complex gives the desired purified product.

The heparin complexes of the present invention can be orally administered, per se, for example, as a lyophilized powder, or in combination with a pharmaceutically acceptable excipient, e.g., with water as a dispersion or in the form of a tablet, and exhibit a sustained systemic anticoagulant effect. Exemplary excipients include inert fillers and binders such as lactose, sucrose, dextrose, sorbitol and cellulose products; disintegrating agents such as starch and soy polysaccharide; and lubricants such as magnesium stearate, stearic acid and hydrogenated vegetable oils.

Additionally, encapsulation of the complex in an enteric coating, by means well-known in the art, provides a suitable form for oral administration.

The heparin complexes of the present invention may also be administered in the form of a vaginal or rectal suppository, cream or ointment. The formulation of such suppositories, creams and ointments can be accomplished by techniques well known in the art.

Typically, the heparin complexes of this invention are used in amount to provide a dosage of 1400 units of heparin per kg of body weight every 8 to 12 hours. This dosage being sufficient to exhibit a sustained systemic anticoagulant activity.

It has also been found that when the heparin complexes of the present invention are prepared with a stoichiometric excess of quaternary ammonium ion being present in the final product, the ease of absorption of heparin through the intestine is increased. Typically, the heparin complex will contain between five moles of quaternary ammonium ion per mole of heparin tetrasaccharide unit and three parts by weight of quaternary ammonium ion per one part by weight of heparin.

Unlike the surfactants of the prior art, the above-noted formulations are "soft" or "pseudo" quaternary ammonium ions. That is, they will be deproponated in vivo as in the formula I ions, and/or hydrolyzed in vivo to give protonated triethyl amine, a fatty acid and an aldehyde molecule as in the formula II ions. Consequently, they are non-toxic and eminently suited for oral administration.

Turning to the biologically active peptide and protein complexes of the present invention these are formed by reacting an ammonium ion having one of the structural formulas I-V with the alkyl sulfate in an amine to alkyl sulfate ratio of 1:0.3 to 1:1 molar ratio preferred.

Since a soft quaternary ammonium ion is a positively charged reagent and since the alkyl sulfate is a negatively charged reagent, a 1:1 molar ratio of the soft quaternary ammonium ion with the alkyl sulfate is preferred. However, other ratios are possible and fall within the scope of the invention. Ratios of amine to alkyl sulfate in the range from 1:0.3 to 1:1 are contemplated by the present invention. Such ratios are obtained by using an excess of the core complex or the amine/ammonium ion component during formation of the electrostatic complex.

The final electrostatic peptide or protein complex is formed by adding the soft quaternary ammonium ion to an aqueous solution containing a protein.alkyl sulfate complex (i.e., the core complex). The resulting electrostatic complex comprising the entire protein.alkyl sulfate.quarternary ammonium ion complex can be isolated by extracting the aqueous solution with chloroform or another non-polar solvent immiscible with water. The presence of protein in the extracted complex can be verified using the Fluorescamine protein test as described in Udenfried et al, *Science,* 178, 871–872 (1972), which is herein incorporated by reference. When working with a previously untried complex, this allows easy verification of the formation of the desired complex.

This invention may be carried out either by preparing a pharmaceutical composition which may be stored in that form or by producing the sandwich complex immediately prior to administration. When a protonated amine is used to form the final complex, the complex can be stored at approximately 4° C. in 0.005M phosphoric acid for at least 2 weeks. When a soft quaternary ammonium ion is used, the complex should be prepared in deionized water at a pH of approximately 7. It can then be lyophilized and stored in powder form for at least several months. Since oral administration is the principal contemplated end use of the compositions of the present invention, compositions suitable for oral ingestion are preferred storage forms. Such compositions can contain pharmaceutically acceptable carriers in addition to the previously disclosed ingredients. Suitable pharmaceutical carriers include liquid or solid carriers of pharmaceutically acceptable or otherwise inert materials which may be used orally. Examples of liquids are water and aqueous solutions of non-toxic salts, such as sterile physiological solutions of saline, or aqueous solutions containing non-toxic orgnanic solvents, such as ethanol, used to increase the amount of complex in solution. Dilute aqueous solutions of mineral acids having a pH of less than 4 are also suitable. Phosphoric, sulfuric, and hydrochloric acids are preferred. Also suitable are emulsions, such as oil-in-water emulsions. Solutions of non-toxic organic liquids, such as ethanol, are also suitable. Solid carriers include both nutritive carriers, such as sucrose or gelatin, and non-nutritive carriers, such as cellulose or talc. A pharmaceutical preparion of the invention may be in the form, for example, of a liquid, a capsule, a tablet, or a suppositroy.

Pharmaceutical compositions according to the present invention are administered in dosages which depend upon the effect desired for the biologically active compound which is being administered. The determination of the effective amount of the biological compound is not considered to be part of the present invention since dosage rates are generally determined by the effect of the composition on the particular patient taking the medication. An amount equal in dose rate (mg/kg) to the amount normally injected parenterally for known biologically active peptides is suitable for use in the present invention as an initial dose and may be adjusted as necessary to achieve the desired effect.

A particularly preferred embodiment of this invention comprises enterally administering a sandwich complex of the invention containing insulin as the active ingredient to produce a hypoglycemic effect. The amount required will depend on the severity of the diabetes and on the condition of the patient (e.g., time since ingestion of food, type and amount of food ingested, etc.). Adjustment of the amount required to maintain the proper blood glucose level is within the capability of those of ordinary skill in the art. An orally administered sandwich complex (of insulin or any other active peptide) is especially preferred.

The above disclosure generally describes the present invention. A more complete understanding can be obtained by reference to the following specific examples which are provided herein for purposes of illustration only and are not intended to be limiting unless otherwise specified.

EXAMPLE 1

Synthesis of 1,3-Benzylidene glycerol

A mixture of glycerol (15 g, 0.163 mole) and a slight excess of benzaldehyde (18.7 g, 0.175 mole) in 60 ml of toluene with a catalytic amount of p-toluenesulfonic acid (0.3 g) was refluxed and stirred for 5 hr. in a Soxhlet apparatus containing dry $MgSO_4$ for removal of water. The products, a mixture of 1,3 and 1,2-benzylidineglycerols was obtained by distillation under reduced pressure. The reaction products were separated on a Florisil column (1.5×42 cm) and eluted with n-hexane:ether 90:10 (100 ml), 70:30 (350 ml), 50:50 (450 ml) and 0:100 (300 ml). The desired product 1,3-benzylideneglycerol was derived as a crystalline product in 70:30, 0:100 elution, the only product of the 50:50 eluting solvent was the 1,2 isomer. The 1,3-benzylideneglycerol (MP 50°–60° C.) was further purified by recrystallizing the combined crystalline products from benzene-petroleum ether (m.p. 82°–83° C.).

EXAMPLE 2

Synthesis of 1-3-benzylidene glycerol

The procedure of Example 1 was repeated except that dihydroxyacetone replaced glycerol. The resultant product of this reaction was 5-oxo-2-phenyl-1,3-dioxane. Since the dioxane is the sole product of this reaction no column separation was required. The dioxane was reduced to 1,3-benzylidene glycerol by reaction with sodium borohydride followed by in-situ reaction with sodium hydroxide.

EXAMPLE 3

Synthesis of 1,3-benzylidene glycerol ether 1,3 Benzylideneglycerol formed in Example 1 or 2 was added in portions at 1:1 mole ratio to vigorously stirred, finely powdered potassium in xylene (0.1 mole of reaction mixture in 300 ml of xylene) (52) and the reaction continued with refluxing and stirring. Excess dimethylaminoethyl chloride (0.175 mole) was added in portions accompanied by refluxing and stirring. This reaction continued for 20 hours. After cooling, potassium chloride was removed via filtratipon and the filtrate was evaporated under reduced pressure to remove xylene and unreacted dimethylaminoethyl chloride. The residue was distilled to remove the unreacted 1,3-benzylideneglycerol. The 1,3-benzylideneglycerol ether was obtained by crystallizing the residue from ethanol.

EXAMPLE 4

Synthesis of the Ammonium having Structural Formula I

An appropriate amount α-chlormethyl ester [RC(O)OCH$_2$Cl] (or -chloroethyl ester [RC(O)OCH(CH$_3$)Cl]) of a saturated (or unsaturated) fatty acid having 18 carbon atoms using the method of Bohr et al (*J. Med Chem* 23, 469–474, 1980) was added dropwise in a 1:1 mole ratio to a vigorous stirred solution of 1,3-N,N-dimethylbenzylideneglycerol-ethylamine in dry petroleum ether under a nitrogen atmosphere. Refluxing and stirring was continued until the reaction was complete. The solvent was then evaporated under reduced pressure, and the desired products were obtained either via column chromatography (florisil) or crystallization from the appropriate solvent.

The benzylidene blocking group of the desired product was removed by heating the benzylideneglycerol ester (0.01 mole) andfinely powdered boric acid (0.1 mole) at a 1:10 mole ratio in an appropriate volume of 2-methoxy ethanol, ca. 20 ml, for 30 min to one hr. A small amount of boric acid remained undissolved. The mixture was dissolved in ether and washed with water, then the ethereal solution was dried ($Na_2SO_4$). The residue was isolated and purified via crystallization from ether.

EXAMPLE 5

Synthesis of 2-glycerol phosphoryl chloride 1,3-benzylideneglycerol, obtained in Example 1 or 2 was phosphorated with phosphorous oxychloride (one molar equivalent) in the presence of quinoline. The resulting phosphatidic acid chloride was esterfied with choline iodide (1.125 molar equivlent) in the presence of pyridine. The reaction mixture was separated by column chromatography on silicic acid to give 1,3-benzylideneglycerophosphoryl choline. The benzylidene protecting group was removed by heating the above product with powdered boric acid in 2-methoxyethanol to give the desired 2glycerolphosphoryl choline iodide.

EXAMPLE 6

Thoracic Duct Cannulation of Rats

Three rats were fed 1 ml of corn oil via gavage. Three hours later, thoracic duct cannulatin and feeding duodenostomy was performed under ether anesthesia. The body temperature of the rats were maintained at 36°–38° C. during and after the operation. The thoracic duct fistula consisted of three parts, i.e. the main body—a 30 cm PE 160 tubing (id 1.14 mm, od 1.57 mm) with a U-shape bent at one end, (the short arm is about 1 cm long), a 7.5–5 mm tip made of PE 60 tubing (id 0.76 mm, od, 1.22 mm) and a 30 cm of PE 10 (id, 0.28 mm, od, 0.61 mm) inserted atthe bend and glued onto the PE 160 tubing as a side arm for a slow, continuous infusion of anticoagulant solution.

Cannulation of the thoracic duct was accomplished through an incision just distal to the last rib, extending from the midling anteriorly of the left quadratus lumboram muscle posteriorly. A small gauze pack wetted with isotonic saline was placed such that it pushed the stomach, liver, and intestine back and to the right, exposed the diaphragm, the aorta, and the left adrenal gland and kidney. Retractors were used to retract the kidney distally and to hold the incision open. With the use of a blunt, curved microforcep, a small opening was made in the peritoneum over the quadratus lumborum, approximately 0.5 cm cephalad to the superior suprarenal artery. The vein and peritoneum were dissected superficially and retracted to the right until the left subcostal artery was exposed. The thoracic duct was visible just posterior to the aorta, appeared to be opaque due to the presence of corn oil. It was 1 to 2 mm. in diameter and was embedded in loose connective tissue and fat. The thoracic duct was exposed for a length of 5 to 8 mm by gently blunt dissection, and was ligated at the upper end of the exposed portion just 3 to 5 mm cauded to the subcoastal artery. After one or two minutes, the portion of thoracic duct at the point of ligation was expanded or ballooned with a milky lymphatic liquid, the sharp tip of the thoracic fistula was then inserted into the swelling and the opaque lymph fluid immediately filled the fistula. The fistula was held in place with a cyanoacrylate adhesive.

The duodenal cannula comprised a PVC tubing (20 cm long, with is 1.10 mm and of 1.50 mm) with a 3–5 mm sleeve which was made of tycon tubing (id 1.56 mm, od 3.13 mm) and glued at one end of the tube. The feeding duodenostomy was accomplished by inserting the cannula at the sleeved end in a distal direction through te stomach and into the duodenum. The duodenal cannula was tied firmly in position with purse string switch; and the tycon sleeve further helped the cannula stay within the gastroduodenal tract.

EXAMPLE 7

At the end of the operations of Example 6, the skin incisions were closed. Body temperature of the rats were maintained at 36°–38° C. during and after the operation.

Postoperatively, the rats were placed in restraining cages overnight and given free access to an aqueous solution containing dextrose 100 g, NaCl 5 g, and KCl 0.4 g/l. An amino acid/carbohydrate mixture (Vivonex, 0.5 strength, Eaton Laboratories) was pumped into the duodenum at 3 ml/hr. Anticoagulant solution (sodium citrate) was also pumped into the thoracic fistula via the PE 10 side-arm at 0.8–1 ml/hr. If the lymph flow was less than 2 ml/hr, the rat was discarded.

At 12 to 18 hours postoperative, a bolus dose of 2-monoglycerol phosphoryl choline.tritiated haparin complex at a dosage ½ to ⅔ that orally administered in Comparative Example 1 was pumped into the duodenum. Afterwards, the pumping of Vivonex into the duodenum resumed at 3 ml/hr. Lymph fluid was continuously collected for 24 hours using a Gilson fraction collector at 30 minutes per fraction. The fractions were counted in a xylene in a xylene-based scintillant (Instagel, Packard Inst.). The lymph anticoagulant activity was determined by the activated partial thromboplastin time (APTT) test. This test determines the time for recalcified plasma to clot after incubation with a reagent comprising a platelet phospholipid and a contact activator which is a measure of the rate at which thrombin is formed via the intrinsic pathway of coagulation. For up to 24 hours anticoagulant activity was observed. Actual coagulant effect on the three rats operated on in accordance with Example 6 is summarized in Table I below.

The rats were sacrificed after 24 hours. The intestine with mesentary and lumenal content, from the esophagus to the rectum including the stomach, was removed and homogenized (GI tract homogenate). The spleen, liver, kidney, heart and lung were homogenized individually. Aliquots of each homogenate (digested in NC5 Amersham/Searle) were counted in a scintillant containing PPO (2,5-diphenyl oxazole) (6 g) and POPOP (1,4-bis[2-(5-phenyl oxazolyl)benzene], (75 mg)/liter of toluene.

The amount of tirtuated ($^3H$) heparin complex (HC) infused (D) is equal to the dosage given.

The amount of $^3H$-heparin complex (HC) infused (D) is equal to the dosage given. The amount of $^3H$ activity in the lymph ($HD_{lym}$) was measured directly as is that remaining in the GI Tract homogenate ($HC_{gi}$). It is assumed that $^3$H-heparin complex, which is absorbed but not recovered, is transported via the portal venous circulation.

$$D - HC_{gi} = HC_{(transported + absorbed)} = HC_{lym} + HC_{portal\ vein}$$

$$\%\ recovery\ from\ lymph = \frac{HC_{lym}}{D - HC_{gi}} \times 100\%$$

% transported via portal vein circulation =

$$\frac{D = HC_{gi} = HC_{lym}}{D = HC_{gi}} \times 100\%$$

From this data the % heparin complex transported in the lymph and % heparin complex remaining in the gastro-intestinal tract is determined. This data is included in Table 2.

TABLE 1

| Rat No. | 155 | 160 | 161 |
|---|---|---|---|
| Rat Wt., g | 420.8 | 413 | 291 |
| Dosage, mg/kg | 5.76 | 12.5 | 12.5 |
| Lymphatic Fluid Anticoagulant Activity (units/ml) | | | |
| Time After Administration | | | |
| 0.5 | 0.0761 | 0.0682 | 0.0495 |
| 1.0 | .1230 | .1972 | .1150 |
| 1.5 | .0949 | .2601 | .1500 |
| 2.0 | .1695 | .2643 | .1960 |
| 2.5 | .1602 | .3089 | .1960 |
| 3.0 | .1879 | .3628 | 0 |
| 3.5 | .1136 | .1972 | .1090 |
| 4.0 | .0977 | .1972 | .0495 |
| 4.5 | .0949 | .2685 | .2810 |
| 5.0 | .0761 | .4668 | .1555 |
| 5.5 | .1695 | .3015 | .0793 |
| 6.0 | .2337 | .2809 | .921 |
| 6.5 | .1136 | .3089 | .0615 |
| 7.0 | .1695 | .3506 | 0 |
| 7.5 | .1416 | .3262 | 0 |
| 8.0 | .0191 | .3311 | .0675 |
| 8.5 | .2791 | .2643 | .0615 |
| 9.0 | .2337 | .2435 | .0195 |
| 9.5 | .2610 | .2435 | .0075 |
| 10.0 | .2790 | .3506 | 0 |
| 10.5 | .2790 | .4311 | .1206 |
| 11.0 | .2337 | .4311 | .0795 |
| 11.5 | .2610 | .2850 | .1265 |
| 12.0 | .1230 | .2850 | .1090 |
| 12.5 | .2610 | .3830 | .0971 |
| 13.0 | .1250 | .4826 | .1355 |
| 13.5 | .2063 | .3850 | .1380 |
| 14.0 | .3061 | .4232 | .1670 |
| 14.5 | .2155 | .3425 | .0971 |
| 15.0 | .2701 | .3180 | .1555 |
| 15.5 | .2791 | .3056 | .0375 |
| 16.0 | .4108 | .2183 | .2360 |
| 16.5 | .4108 | .3871 | .0075 |
| 17.0 | .1695 | .3261 | 0 |
| 17.5 | .2063 | .7486 | .2360 |
| 18.0 | .1695 | .2225 | .0855 |
| 18.5 | .1230 | .1845 | 0 |
| 19.0 | .0572 | .3256 | .3475 |
| 19.5 | ND | .3830 | .3200 |
| 20.0 | ND | .6265 | .2530 |
| 20.5 | ND | .5256 | .3090 |
| 21.0 | ND | .3871 | .2416 |
| 21.5 | ND | .4311 | .0971 |
| 22.0 | ND | .3233 | .0910 |
| 22.5 | ND | ND | .0795 |
| 23.0 | ND | ND | .3910 |
| 23.5 | ND | ND | .2917 |
| 24.0 | ND | ND | .2415 |
| Anticoagulant Activity of Plasma of Sacrificed Rat | .3330 | ND | .1960 |

TABLE 2

| Rat No. | 155 | 160 | 161 |
|---|---|---|---|
| Tritiated Heparin Complex Transported in Lymph, % | 74.30 | 23.87 | 20.53 |
| Tritiated Heparin Complex Remaining in Gl Tract % | ND | 4.94 | 11.87 |

COMPARATIVE EXAMPLE 1

Oral Administration of Heparin

Commercially available heparin was orally administered to a group of rats. Six rats were employed in this study. They had an average weight of 415.5 grams with a standard deviation of 47.1 grams. The heparin orally administered dosage averaged 3992 units per kilogram with a standard deviation of 373 units per kg with a standard deviation of 2.39 mg/kg. The anitcoagulant activity, measured by the APTT method, was measured as a function of time and is summarized in Table 3 below.

TABLE 3

| Time After Oral Heparin Administration, hr | Anticoagulent Activity, unit/ml |
|---|---|
| 0 | 0 |
| .25 | .03 ± .04 |
| .50 | .03 ± .05 |
| .75 | .05 ± .06 |
| 1.00 | .03 ± .05 |
| 1.50 | .03 ± .06 |
| 2.0 | .03 ± .06 |
| 3.0 | .02 ± .04 |
| 4.0 | 0 |
| 5.0 | .03 ± .04 |
| 6.0 | 0 |
| 7.0 | 0 |

The above embodiments and examples are given to illustrate the scope and spirit of the present invention. These embodiments and examples will make apparent, to those skilled in the art, other embodiments and examples. These other embodiments and examples are within the contemplation of the instant invention. Therefore, the invention should be limited only by the amended claims.

What is claimed is:

1. A compound selected from the group consisting of

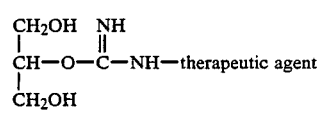

where the therapeutic agent is heparin, a biologically active peptide or protein or a protein antineoplastic agent possessing amine functionality; and

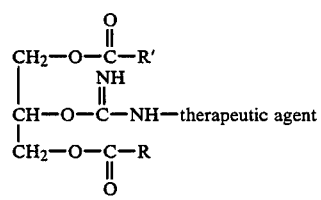

where R and R' are the same or different and are saturated or unsaturated aliphatic containing at least 10 carbon atoms; and the therapeutic agent has the meanings given above.

* * * * *

UNITED STATES PATENT AND TRADEMARK OFFICE
CERTIFICATE OF CORRECTION

PATENT NO.  :  4,820,811                    Page 1 of 3
DATED       :  April 11, 1989
INVENTOR(S) :  Lin-nar L. Teng It is certified that error appears in the above-identified patent and that said Letters Patent is hereby corrected as shown below:

On the title page:

In the Abstract, column 2, line 26: "$R^1$ having the" should read as --$R^1$ have the--

Column 7, line 21: "selecte" should read as --selected--

Column 8, line 64: "adenophypophyseal" should read as --adenohypophyseal--

Column 8, lines 64-65" "corticotropinm" should read as --corticotropin--

Column 9, line 1: "factorm" should read as --factor--

Column 9, line 34: "fior" should read as --for--

Column 12, line 31: "te" should read as --the--

Column 14, line 2: "mau" should read as --may--

Column 14, line 52: "I-V" should read as --I-IV--

UNITED STATES PATENT AND TRADEMARK OFFICE
CERTIFICATE OF CORRECTION

PATENT NO. : 4,820,811
DATED : April 11, 1989
INVENTOR(S) : Lin-nar L. Teng

It is certified that error appears in the above-identified patent and that said Letters Patent is hereby corrected as shown below:

Column 14, line 53: "1:1 molar ratio preferred." should read as --1:1 with a 1:1 molar ratio preferred.--

Column 15, line 43: "suppositroy." should read as --suppository.--

Column 16, line 51: "filtratipon" should read as --filtration--

Column 16, line 59: "Ammonium having" should read as --Ammonium ion having--

Column 17, line 49 "andfinely" should read as --and finely--

Column 17, line 45: "atthe" should read as --at the--

Column 18, line 13: "te" should read as --the--

Column 18, line 67: "$(HD_{lym})$" should read as --$(HC_{lym})$--

UNITED STATES PATENT AND TRADEMARK OFFICE
CERTIFICATE OF CORRECTION

PATENT NO. : 4,820,811

DATED : April 11, 1989

INVENTOR(S) : Lin-nar L. Teng

It is certified that error appears in the above-identified patent and that said Letters Patent is hereby corrected as shown below:

Column 19, lines 11-12:
$$" \frac{D = HC_{gi} = HC_{lym}}{D = HC_{gi}} \times 100\% "$$

should read as:
$$-- \frac{D - HC_{gi} - HC_{lym}}{D - HC_{gi}} \times 100\% --$$

Signed and Sealed this

Third Day of April, 1990

*Attest:*

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,820,811
DATED : April 11, 1989
INVENTOR(S) : Lin-nar L. Teng It is certified that error appears in the above-identified patent and that said Letters Patent is hereby corrected as shown below:

On the Title Page, before Section [54] insert the following: --"This invention was made with government support under grant number R01 HL 22035 awarded by the National Institutes of Health. The government has certain rights in the invention.--"

Signed and Sealed this

Seventh Day of September, 1993

Attest:

BRUCE LEHMAN

*Attesting Officer*     *Commissioner of Patents and Trademarks*